(12) United States Patent
Guha et al.

(10) Patent No.: US 9,439,947 B2
(45) Date of Patent: Sep. 13, 2016

(54) THERAPY FOR RADIATION-INDUCED LUNG INJURY

(71) Applicant: ALBERT EINSTEIN COLLEGE OF MEDICINE, INC., Bronx, NY (US)

(72) Inventors: Chandan Guha, Scarsdale, NY (US); Subhrajit Saha, Bronx, NY (US)

(73) Assignee: Albert Einstein College of Medicine, Inc., Bronx, NY (US)

(*) Notice: Subject to any disclaimer, the term of this patent is extended or adjusted under 35 U.S.C. 154(b) by 0 days.

(21) Appl. No.: 14/666,746

(22) Filed: Mar. 24, 2015

(65) Prior Publication Data
US 2015/0306177 A1    Oct. 29, 2015

Related U.S. Application Data

(60) Provisional application No. 61/971,600, filed on Mar. 28, 2014.

(51) Int. Cl.
*A61K 38/00* (2006.01)
*A61K 38/17* (2006.01)
*C07K 14/435* (2006.01)
*C07K 14/075* (2006.01)
*A61K 35/761* (2015.01)
*A61K 48/00* (2006.01)

(52) U.S. Cl.
CPC ......... *A61K 38/1709* (2013.01); *A61K 35/761* (2013.01); *A61K 48/00* (2013.01); *C07K 14/075* (2013.01); *C07K 14/435* (2013.01)

(58) Field of Classification Search
CPC ............. A61K 48/00; A61K 38/1709; A61K 35/761; C07K 14/00; C07K 14/075; C07K 14/435
See application file for complete search history.

(56) References Cited

U.S. PATENT DOCUMENTS

2010/0183749 A1    7/2010  Brey

OTHER PUBLICATIONS

Zhao, J. et al. R-Spondin1 protects mice from chemotherapy or radiation-induced oral mucositis through the canonical Wnt/B-catenin pathway. Proc. Natl. Acad. Sci. USA, 2009, vol. 106(7), p. 2331-2336.*
Bell S M et al., entitled "R-spondin 2 is required for normal laryngeal-tacheal, lung and limb morphogenesis," Development 135, 1049-1058 (2008).
Saha S et al., entitled "R-Spondin1 Mitigates Radiation Induced Pulmonary Syndrome in Mice," European Radiation Research Society Annual Meeting, Sep. 1-5, 2013, Dublin, 2 pages.
Saha S et al., entitled "Bone Marrow Stromal Cell Transplantation Mitigates Radiation-Induced Gastrointestinal Syndrome in Mice," PLoS ONE, Sep. 2011, vol. 6, Issue 9, e24072, pp. 1-23.
Zhou W J et al., entitled "Induction of intestinal stem cells by R-spondin 1 and Slit2 augments chemoradioprotection," Nature, Sep. 5, 2013;501(7465), pp. 1-15.
Bhanja P. et al., entitled "Protective Role of R-spondin1, and Intestinal Stem Cell Growth Factor, against Radiation Induced Gastrointestinal Syndrome in Mice," PLoS ONE, Nov. 2009, vol. 4, Issue 11, e8014, pp. 1-10.

* cited by examiner

*Primary Examiner* — Robert Landsman
*Assistant Examiner* — Bruce D Hissong
(74) *Attorney, Agent, or Firm* — Amster, Rothstein & Ebenstein LLP

(57) ABSTRACT

Methods are disclosed for therapy of radiation-induced lung injury and other lung diseases using R-spondin1.

9 Claims, 7 Drawing Sheets

SEQUENCE LISTING

<160> NUMBER OF SEQ ID NOS: 1

<210> SEQ ID NO 1
<211> LENGTH: 263
<212> TYPE: PRT

```
<213> ORGANISM: Homo sapiens

<400> SEQUENCE: 1

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
            115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
            195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260
```

THERAPY FOR RADIATION-INDUCED LUNG INJURY

CROSS-REFERENCE TO RELATED APPLICATION

This application claims the benefit of U.S. Provisional Patent Application No. 61/971,600, filed Mar. 28, 2014, the contents of which are herein incorporated by reference in their entirety.

STATEMENT OF GOVERNMENT SUPPORT

This invention was made with government support under grant number AI091175 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Radiation-induced pulmonary syndrome (RIPS) is a delayed lethal event from accidental or intentional exposure to irradiation in case of nuclear accidents or terrorism. In the event of a nuclear accident or deliberate attack resulting in a large population exposure to ionizing radiation, victims will need to be triaged according to the severity of acute radiation illness. Radiation-induced bone-marrow syndrome and gastrointestinal (GI) syndrome occur at lower doses of radiation and have an earlier onset than does radiation-induced pulmonary syndrome. Although acute lung injury is not an early event compared to radiation-induced gastrointestinal and hematologic disorder, successful treatment of gastrointestinal and hematologic syndromes do not rescue patients completely as mortality from respiratory distress at late time point is always an issue. Furthermore, many victims at risk for development of chronic injury will not be symptomatic for months to years after exposure. Therefore, it is necessary to develop a therapeutic strategy that is effective when delivered after the onset of symptomatic injury. Radiation-induced acute lung injury results from a combination of direct cytocidal effects on pneumocytes, generation of free radical and development of sepsis.

Two phases of radiation lung injury have been described. Acute radiation pneumonopathy (pneumonitis) can occur from several weeks to 6 months post-irradiation. If a large volume of lung has been affected, this phase can be life threatening. In late radiation-induced lung injury, occurring months to years after irradiation, the number of inflammatory cells decreases and deposition of collagenous occurs, resulting in irreversible lung fibrosis.

The present invention addresses the need for methods for therapy of subjects for radiation-induced pulmonary syndrome, as well as other pulmonary diseases.

SUMMARY OF THE INVENTION

The present invention provides methods for treating a subject with a radiation-induced lung injury or at risk for a radiation-induced lung injury comprising administering to the subject R-spondin1 in an amount effective to treat or prevent a radiation-induced lung injury.

The invention also provides methods for treating a subject with emphysema, chronic obstructive pulmonary disease (COPD) or fibrosis not due to radiation-induced lung injury comprising administering to the subject R-spondin1 in an amount effective to treat emphysema, COPD, or fibrosis.

DETAILED DESCRIPTION OF THE INVENTION

Figure 1:
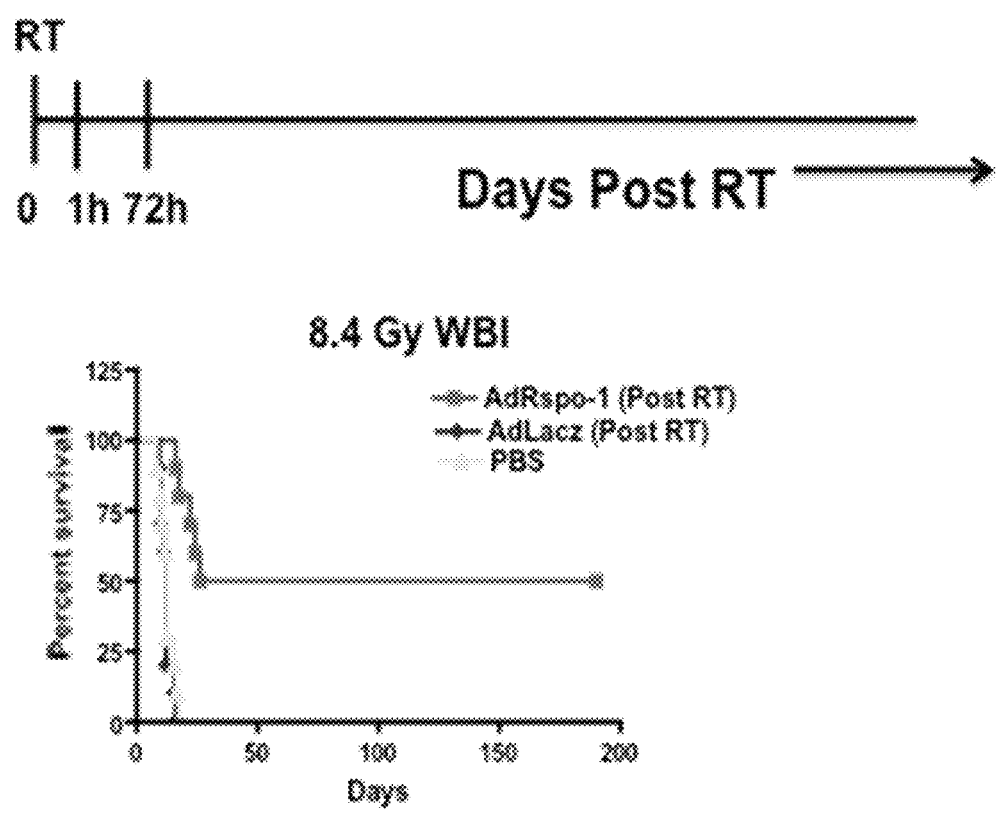
FIG. 1. AdRspo-1 improves survival of mice after whole body irradition. Mice were treated with $5 \times 10^9$ particles of AdRspo1 (adenovirus expressing human R-spondin1 protein) or AdLacZ (adenovirus expressing β-galactosidase gene of *E. coli* as control) or with phosphate buffered saline (PBS) 1 hour and 72 hours after radiation treatment (RT) with 8.4 Gy whole body radiation (WBI). Mice treated with AdRspo1 had enhanced survival compared to mice treated with AdLacZ or PBS.
Figure 2:
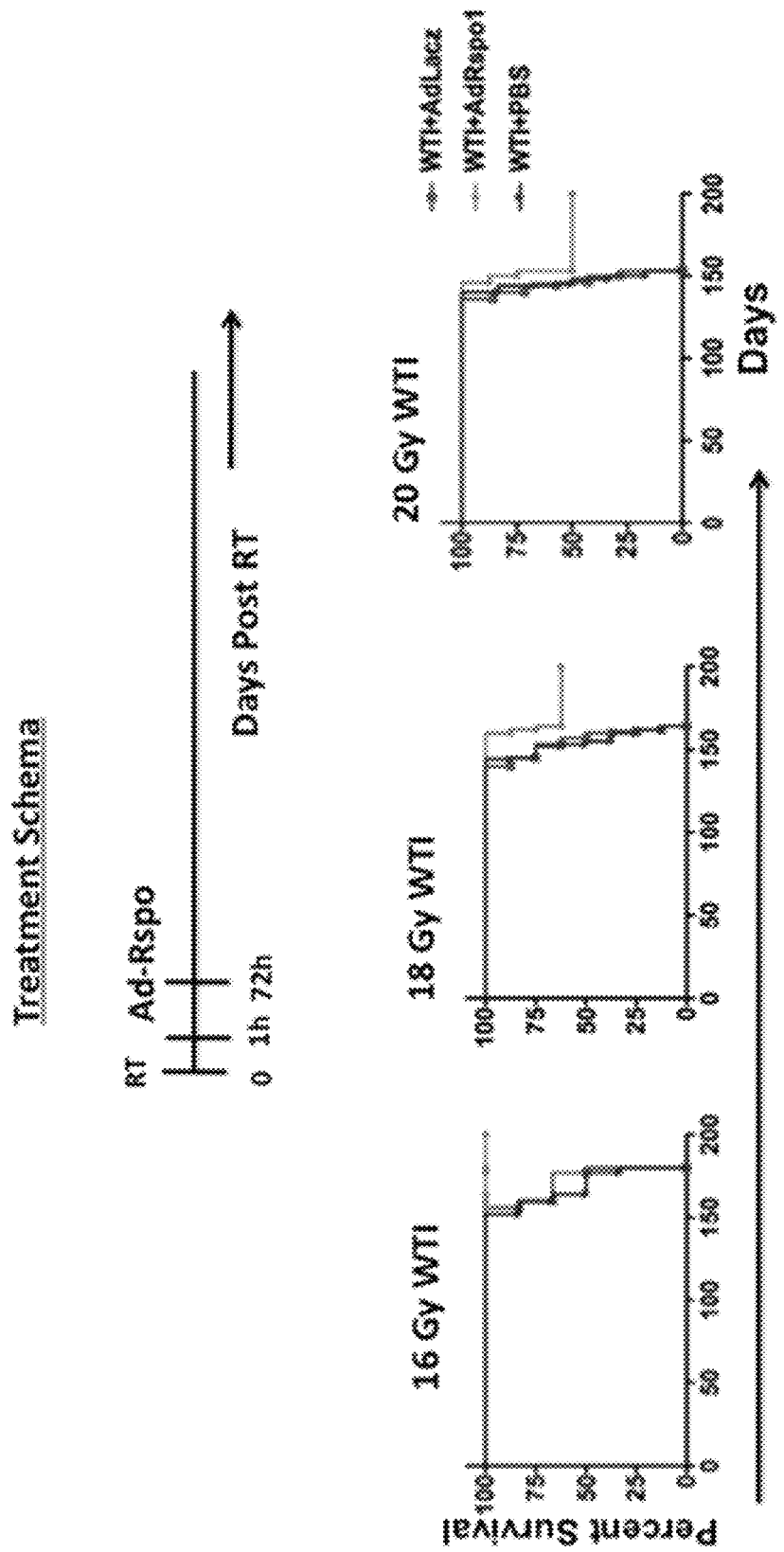
FIG. 2. AdRspo-1 mitigates radiation-induced pulmonary syndrome (RIPS). AdRspo-1 treatment improves survival in mice exposed to whole thorax irradiation (WTI) (16-20 Gy). Mice treated with AdRspo1 had enhanced survival compared to mice treated with AdLacZ or PBS.
Figure 3A:
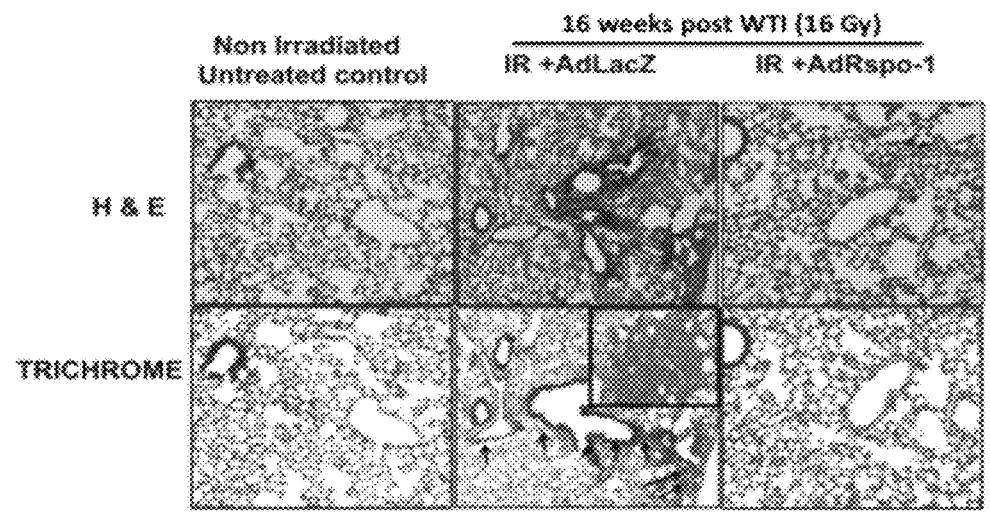
FIG. 3A. AdRspo-1 mitigates RIPS. AdRspo-1 induces structural regeneration of pulmonary epithelium and inhibits collagen deposition in irradiated lung. H&E—Hematoxylin and eosin stain.
Figure 3B:
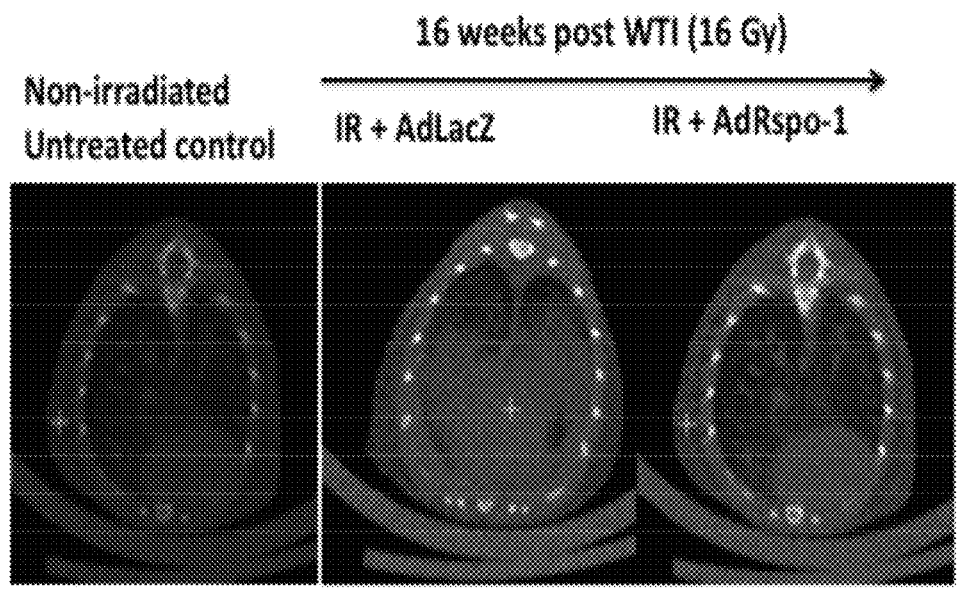
FIG. 3B. AdRspo-1 mitigates RIPS. CTSCAN analysis demonstrated that AdRspo-1 treatment reduces pulmonary density compared to irradiated control.
Figure 3C:
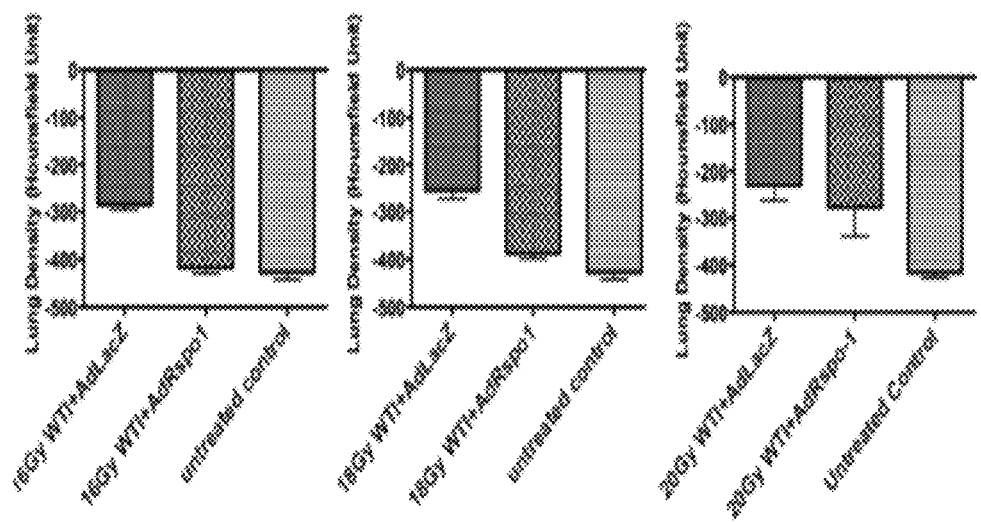
FIG. 3C. AdRspo-1 mitigates RIPS. CTSCAN analysis demonstrated that AdRspo-1 treatment reduces pulmonary density compared to irradiated control.
Figure 4A:
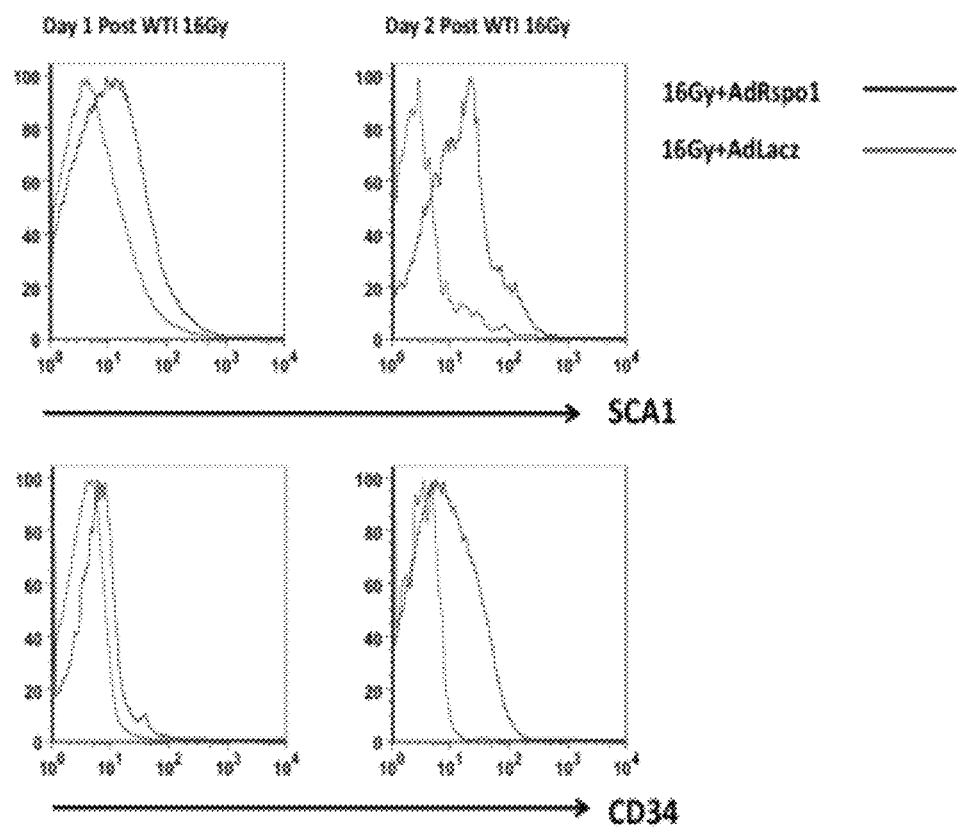
FIG. 4A. AdRspo-1 restituted the bronchioalveolar stem/progenitor cells (BASC) population in irradiated pulmonary epithelium. Flowcytometric analysis showed that expression of BASC markers were reduced at 48 hr after WTI and treatment with AdRspo-1 restitute the expression. AdRspo1 is the right trace in each plot.
Figure 4B:
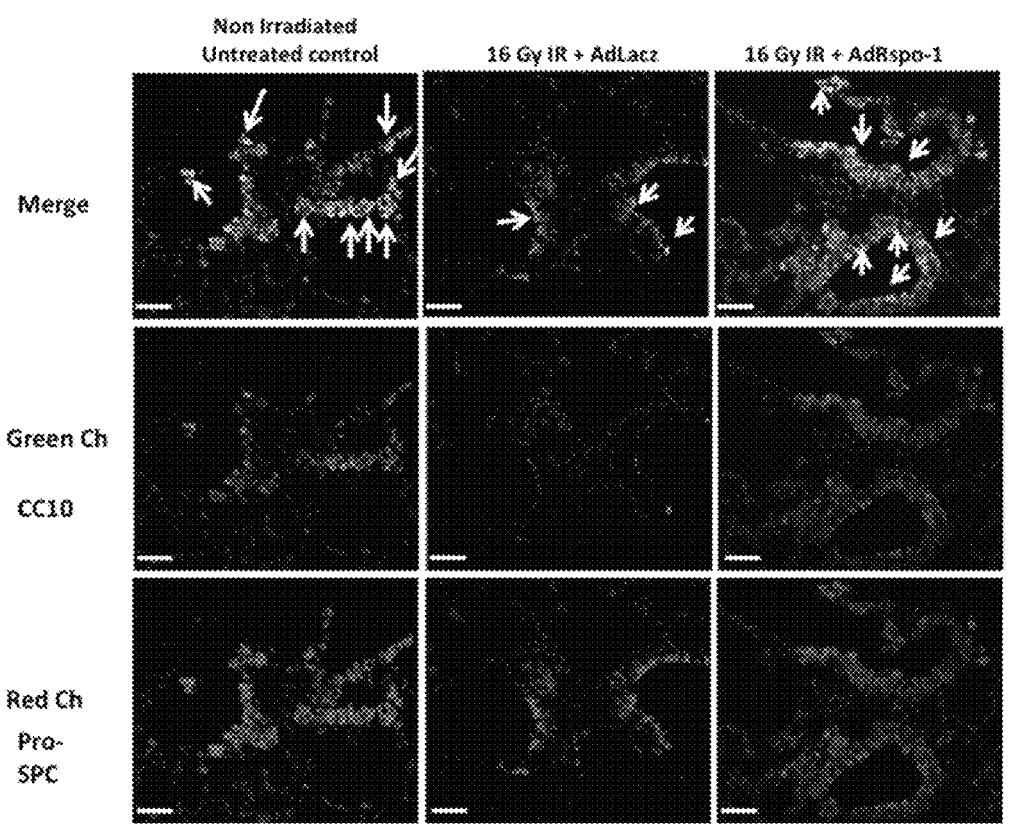
FIG. 4B. AdRspo-1 restituted the bronchioalveolar stem/progenitor cells (BASC) population in irradiated pulmonary epithelium. CC10+ SPC+ BASC cells were more in AdRspo-1 treated group compared to irradiated control (indicated with arrow). Pulmonary epithelium was stained with CC10+ Alexa 488 and SPC Alexa647. Double positive cells were observed.
Figure 5:
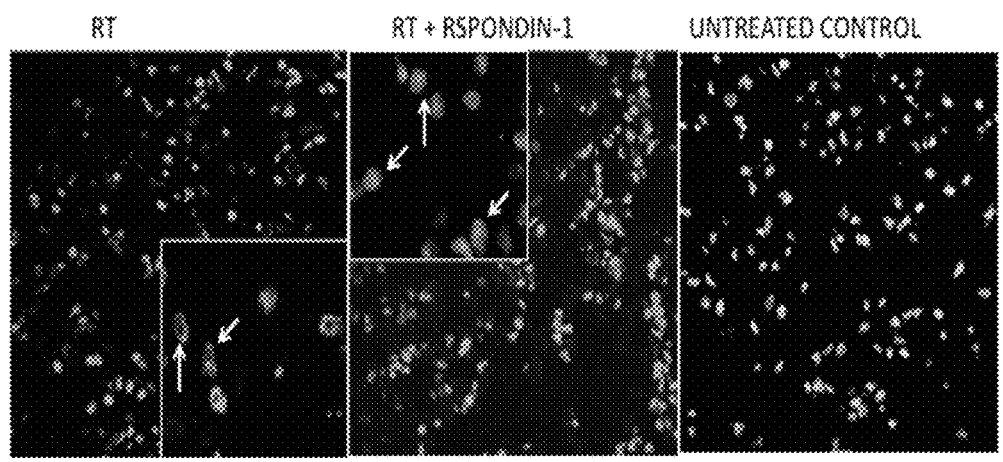
FIG. 5. AdRspo1 treatment in irradiated lung activates β-catenin downstream pathway by activating β-catenin translocation from cytosol to nucleus (marked with arrow). It was noted that in the radiated lung without AdRspo-1 β-catenin were located in cytoplasm (marked with arrow).

The present invention provides a method for treating a subject with a radiation-induced lung injury or at risk for a radiation-induced lung injury comprising administering to the subject R-spondin1 in an amount effective to treat or prevent a radiation-induced lung injury.

Subjects at risk for radiation-induced lung injury include, for example, a patient who is receiving radiation therapy for cancer or other disease, including radiation therapy for lung, mediastinal lymphatics, lung disease, or thoracic or breast cancer; a nuclear power plant worker; a nuclear warfare personnel; and a subject who is or is about to be exposed to elevated levels of radiation due to a nuclear accident, war or terrorist attack.

The present invention is directed to treating or preventing chronic or late effects of radiation-induced injury, for example radiation-induced lung injury that occurs at least 3 months after exposure to radiation or at least 6 months after exposure to radiation.

The invention also provides a method for treating a subject with emphysema, chronic obstructive pulmonary disease (COPD) or fibrosis not due to radiation-induced lung injury comprising administering to the subject R-spondin1 in an amount effective to treat emphysema, COPD, or fibrosis. Preferably administration of R-spondin1 to the subject ameleriorates a sign or symptom of emphysema, COPD, or fibrosis.

R-spondin1 can be administered to the subject using, for example, a viral vector that expresses R-spondin1 protein. The viral vector can be, for example, a lenti virus vector or an adenovirus vector, such as a recombinant adenovirus vector. R-spondin1 can also be administered to the subject, for example, as a protein such as a purified recombinant protein. Preferably, for human subjects, R-spondin1 is a human R-spondin1. Human R-spondin1 can have the amino acid sequence (GenBank: ABC54570.1) (SEQ ID NO:1):

```
  1  mrlglcvval vlswthltis srgikgkrqr risaegsqac akgcelcsev ngclkcspkl 61  fillerndir qvgvclpscp pgyfdarnpd mnkcikckie hceacfshnf ctkckeglyl 121  hkgrcypacp egssaangtm ecsspaqcem sewspwgpcs kkqqlcgfrr gseertrrvl 181  hapvgdhaac sdtketrrct vrrvpcpegq krrkggqgrr enanrnlark eskeagagsr 241  rrkgqqqqqq qgtvgpltsa gpa.
```

R-spondin1 can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. R-spondin1 can be administered systemically or directly to the lungs.

Administration of R-spondin1 to the subject can inhibit or prevent, for example, one or more of radiation-induced pulmonary inflammation, deposition of collagen in the lungs, plural infusion of fluid, and lung fibrosis. Administration of R-spondin1 can prolong survival of a subject exposed to radiation.

The subject can be a mammal, and is preferably a human.

For radiation-induced lung injury, R-spondin1 can be administered, for example, in any one or more of the following time periods: before exposure to radiation to prevent radiation-induced pulmonary injury, after radiation exposure but before induction of clinical symptoms of radiation-induced pulmonary injury, and after radiation exposure and appearance of clinical symptoms of radiation-induced pulmonary injury.

In one embodiment, R-spondin1 is administered as the sole therapeutic agent used to treat or prevent lung injury, such as a radiation-induced lung injury.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Previous findings with radiation-induced gastrointestinal (GI) syndrome and bone marrow syndrome suggested that radiation damage above lethal doses is mostly due to stem cell niche disorder. The studies showed that regeneration of host stem cell niche by bone-marrow derived adherent stromal cell (BM-ASC) transplantation 24 hr after lethal doses of whole body irradiation (10-14 Gy) could rescue mice from GI and bone-marrow syndrome. Moreover, survival of those mice beyond 24 weeks post irradiation suggested that they have also overcome the radiation induced pulmonary disorder. On the basis of these observations, the inventors rationalized that radiation-induced acute lung injury is due in part by host stem cell niche disorder and that rapid compensation of their function could facilitate the regenerative and repair process. The inventors hypothesized that regeneration of bronchioalveolar stem/progenitor cells (BASC) might compensate for the loss of irradiated penumocytes, thereby mitigating RIPS. Since activation of the wnt/β-catenin pathway has been implicated in the maintenance and renewal of adult tissue stem cells in multiple organs, including lungs, it was evaluated whether the Wnt agonist, R-spondin1 (Rspo1), which is a stem cell growth factor, could induce BASC and alveolar regeneration and mitigate RIPS.

The present studies were conducted to define the pulmonary stem cell population that is affected by irradiation and examines the hypothesis that restitution and repair of the pulmonary stem cell niche by pulmonary stem cell growth factors and stromal cell transplantation can stimulate regeneration of the pulmonary stem cells and modulate the post-radiation exposure cytokine syndrome and prevent the development of late pulmonary fibrosis in Radiation Induced Pulmonary Syndrome (RIPS).

Methods

C57Bl/6 mice (6-8 weeks old) (NCI-Fort Dietrich, Md.) were exposed to whole body irradiation (WBI) or to whole thorax irradiation (WTI) using a Shephard$^{137}$Cs-ray irradiator at a dose rate of 236 cGy/min following biosafety guidelines of Albert Einstein College of Medicine.

As described in detail previously (Bhanja et al. 2009), human R-spondin1 cDNA (Origene, Rockville, Md.) was subcloned in pShuttle-2 (Clonetech, Mountain View, Calif.), followed by ligation into the Adeno-X viral DNA according to protocols described in the Adeno-XTM expression system (Clonetech, Mountain View, Calif.).

Irradiated animals were treated by i.v. injection of recombinant adenovirus expressing human stem cell growth factor Rspo1 or LacZ (as a control), $5 \times 10^9$ particles/mice, 1 and 72 hrs post-WTI. Animals were observed for survival (Kaplan-Meier), pulmonary density (CT scan) and histopathological analysis (Hematoxylin-eosin and trichrome staining). BASC regenerative response was determined by FACS and immunohistochemistry, using antibodies to CC10, SPC, CD34 and SCA1. Expression of β-Catenin target genes in alveolar epithelium was determined by qRT-PCR.

Results

AdRspo-1 Improves Survival of Mice After Whole Body Irradition

Whole body radiation (WBI) exposure with a dose of 10 Gy or more is lethal for mice, resulting in mortality due to intestinal and bone-marrow injury. The present study tested the role of AdRspo-1 as a mitigating agent against WBI with the dose range of 8.4-10.4 Gy. Adenovirus expressing human R-spondin1 protein (AdRspo1) was constructed and $5 \times 10^9$ particles of AdRspo1 or AdLacZ (adenovirus expressing β-galactosidase gene of *E. coli* as control) were injected intravenously via tail vein, 1 hour and 72 hour after whole body irradiation (WBI). Although R-spondin1 failed to mitigate beyond the dose of 9.4 Gy WBI, significant survival was observed after exposure to 8.4 Gy (p<0.004) (FIG. 1). Survival studies further showed that these mice continued to live beyond 16 weeks post radiation exposure suggesting that the treatment overcame pulmonary injury.

AdRspo-1 Improves Survival of Mice After Whole Thorax Irradiation

Mice receiving single dose of 16 Gy whole thorax irradiation (WTI) after shielding head, neck, abdomen and extremities showed mortality starting at 22 weeks post radiation. However intravenous administration of AdRspo1 at 1 and 72 hour after WTI resulted in 100% survival beyond 22 weeks (P<0.002) suggesting a possible mitigation role of R-spondin1 against RIPS.

Restitution of Pulmonary Stem Progenitor Cells at Early Post-Radiation Time Point Mitigates Radiation-Induced Damage in Lung The histo-pathological analysis along with CT-SCAN at 16-20 weeks post WTI have shown that AdRspo-1 treatment at early post radiation time point mitigates the delayed lethal effect of radiation. The inventors hypothesized that regenerative therapy at early post-irradiation time point will restitute the pulmonary stem progenitor cells to maintain structural and functional homeostasis of pulmonary epithelium and inhibit fibrosis.

Lung contains anatomically and functionally distinct epithelial stem cell populations. A regional pulmonary stem cell population, termed bronchio-alveolar stem cells (BASCs), was isolated. These cells were identified in bronchio-alveolar duct junction and proliferated during epithelial cell renewal in vivo. Considering the possibility that BASCs could be the potential pulmonary epithelial stem cell population, flow cytometric analysis was performed to study the effect of radiation on the BASC population. It was evident from the histogram analysis that expression of CD34 and SCA1, known markers for BASCs, were decreased at 24 hr after 16 Gy whole thorax irradiation compared to AdRspo-1 treated mice suggesting a possible involvement of BASC for structural repair of alveolar epithelium after radiation damage.

An immunohistochemical analysis of pulmonary epithelium was performed with two other BASC markers (CC10+ SPC+) to determine the presence of pulmonary stem progenitor cells in irradiated lung. CC10+ SPC+ broncho alveolar stem cell (BASC) population were restituted in the Ad-Rspo1 treated group compared to an irradiated control suggesting the possible involvement of BASC to mitigate radiation damage in the lung.

AdRspo-1 Activates β-Catenin Pathway in Pneumocytes

Wnt/β-catenin pathway plays a significant role in stem cell self-renewal process to maintain classic stem cell hierarchies. This function is critical in rapidly renewing tissues like intestine. Under resting condition, β-catenin is present in the cytoplasm. Phosphorylation of β-catenin (by GSK-3 kinase) targets the protein to proteosomes where it is degraded. Wnt activation inhibits GSI-3 kinase phosphorylation of β-catenin, preventing β-catenin degradation and allowing for its translocation from the cytoplasm to the nucleus. In the nucleus, β-catenin binds to and activates the TCF/LEF transcription factor complex to induce the expression of wnt-pathway genes, such as, EphB2, EphB3, TCF4 and LEF1. It was reported that stabilization of β-catenin enhances pulmonary epithelial reparative capacity after injury. Immunohistochemistry followed by confocal microscopic analysis showed an increased β-catenin translocation in nucleus (stained yellow) in AdRspo-1 treated mice whereas most of the β-catenin remained in cytosol (stained green in cytosol) in the AdLacz cohort.

In contrast to AdLacZ-treated animals, AdRspo1 treatment restituted BASC and accelerated the recovery of alveolar epithelium in irradiated lungs and reduced peri-alveolar collagen deposition. CT scan demonstrated reduced HU and pulmonary fibrosis in the irradiated lungs of AdRspo1-treated mice (p<0.0004) compared to AdLacZ controls. AdRspo1 treatment improved the survival of mice that received 16-20 Gy cumulative lung irradiation (p<0.004).

CONCLUSIONS

AdRspo1 mitigates RIPS with restitution of the BASC population and reduces the severity of pneumonitis and pulmonary fibrosis, thereby improving survival. This is the first demonstration that regenerative therapy of pulmonary stemiprogenitor cells shortly after irradiation could mitigate pulmonary fibrosis.

REFERENCES

Bhanja P, Saha S, Kabarriti R, Liu L, Roy-Chowdhury N, Roy-Chowdhury J, Sellers R S, Alfieri A A, Gam C. Protective role of R-spondin1, an intestinal stem cell growth factor, against radiation-induced gastrointestinal syndrome in mice. PLoS One. 2009 Nov. 24; 4(11):e8014.

What is claimed is:

1. A method for treating a subject with a radiation-induced lung injury comprising administering to the subject after exposure to radiation R-spondin1 in an amount effective to treat a radiation-induced lung injury occurring at least 3 months after exposure to radiation.

2. The method of claim 1, wherein the subject is a patient who is receiving radiation therapy, a nuclear power plant worker, a nuclear warfare personnel, or a subject who is exposed to elevated levels of radiation due to a nuclear accident, war or terrorist attack.

3. The method of claim 1, wherein the radiation-induced lung injury occurs at least 6 months after exposure to radiation.

4. The method of claim 1, wherein R-spondin1 is administered to the subject using a viral vector that expresses R-spondin1 protein.

5. The method of claim 4, wherein the viral vector is a recombinant adenovirus vector.

6. The method of claim 1, wherein R-spondin1 is administered to the subject as a purified recombinant protein.

7. The method of claim 1, wherein R-spondin1 is a human R-spondin1.

8. The method of claim 1, wherein administration of R-spondin1 to the subject inhibits one or more of radiation-induced pulmonary inflammation, deposition of collagen in the lungs, plural infusion of fluid, and lung fibrosis.

9. The method of claim 1, wherein the subject is a human.

* * * * *